United States Patent [19]

Tajima

[11] Patent Number: 4,492,871
[45] Date of Patent: Jan. 8, 1985

[54] METHOD FOR DETERMINING IMPURITIES IN EPITAXIAL SILICON CRYSTALS

[75] Inventor: Michio Tajima, Yatabemachi, Japan

[73] Assignees: Agency of Industrial Science & Technology; Ministry of International Trade & Industry, both of Tokyo, Japan

[21] Appl. No.: 408,908

[22] Filed: Aug. 17, 1982

[30] Foreign Application Priority Data

Oct. 7, 1981 [JP] Japan .................... 56-159727

[51] Int. Cl.$^3$ .................................. G01N 21/64
[52] U.S. Cl. .................... 250/459.1; 250/492.2; 250/484.1
[58] Field of Search ............... 250/458.1, 459.1, 492.2, 250/484.1, 337; 356/318, 237; 29/574; 357/91

[56] References Cited

FOREIGN PATENT DOCUMENTS

| 55-39628 | 3/1980 | Japan | 250/492.2 |
| 153328 | 11/1980 | Japan | 29/574 |
| 56-07297 | 2/1981 | Japan | 29/574 |
| 254869 | 3/1970 | U.S.S.R. | 250/338 |

OTHER PUBLICATIONS

Merz, "Photoluminescence of Oxygen in ZnTe Introduced by Ion Implantation", App. Phys. Letters, 15 (5), Sep. 1, 1969, pp. 129–131.

White, "Applications of Photoluminescence Excitation Spectroscopy to the Study of Indium Gallium Phosphide Alloys," J. Phys. D: App. Phys., 3, 1970, pp. 1322–1328.

*Primary Examiner*—Alfred E. Smith
*Assistant Examiner*—Carolyn E. Fields
*Attorney, Agent, or Firm*—Schwartz & Weinrieb

[57] ABSTRACT

A laser beam is directed onto an epitaxial silicon crystal grown on a silicon crystal substrate at the temperature of liquid helium and the spectra of the luminescent light radiated from the crystal and the substrate are analyzed to determine the kind and concentration of impurities in the epitaxial silicon crystal. In particular, a photo luminescence intensity ratio of an impurity within the crystal substrate and an impurity within the epitaxial crystal is graphically related to the concentration of the impurity within the epitaxial crystal such that the concentration levels of the impurity within the epitaxial crystal may be determined as a function of the photo luminescence intensity ratio.

5 Claims, 5 Drawing Figures

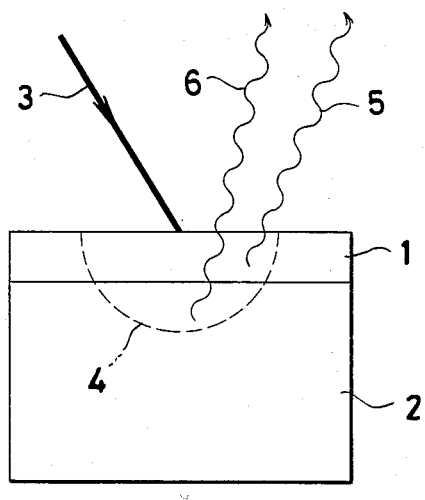
Fig_1
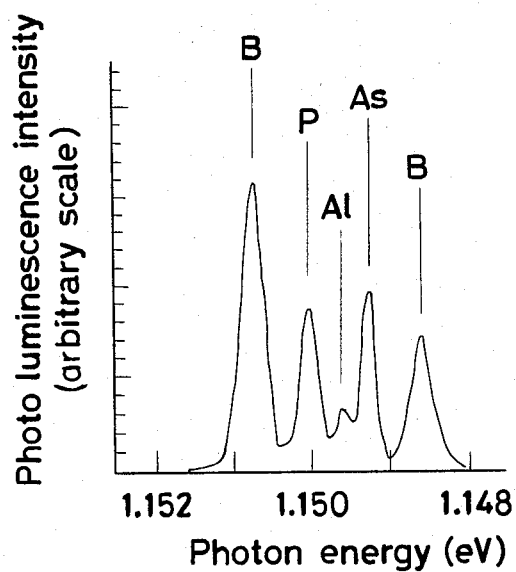
Fig_5
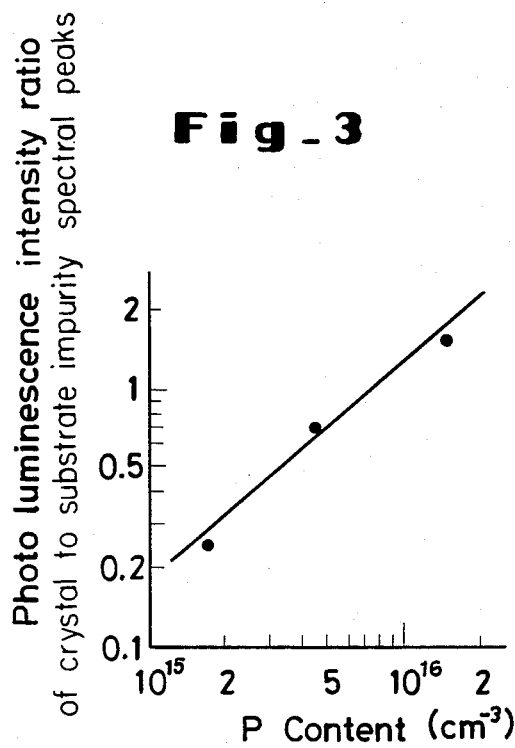
Fig_3
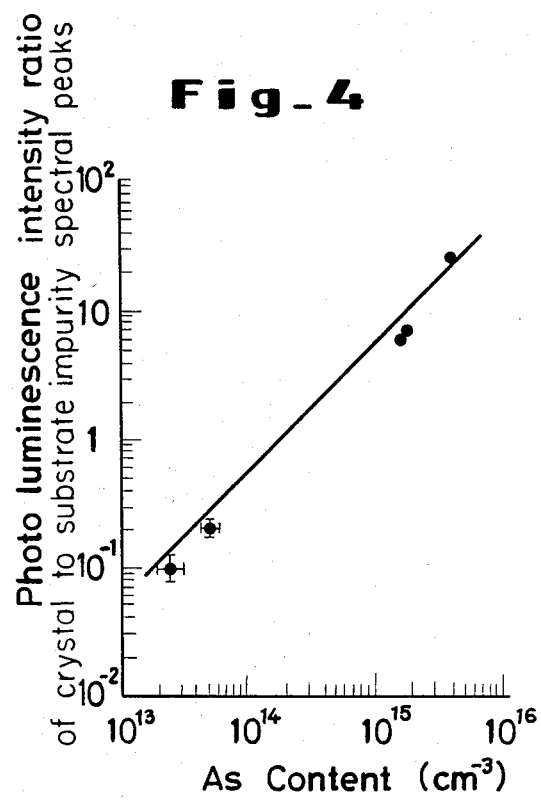
Fig_4

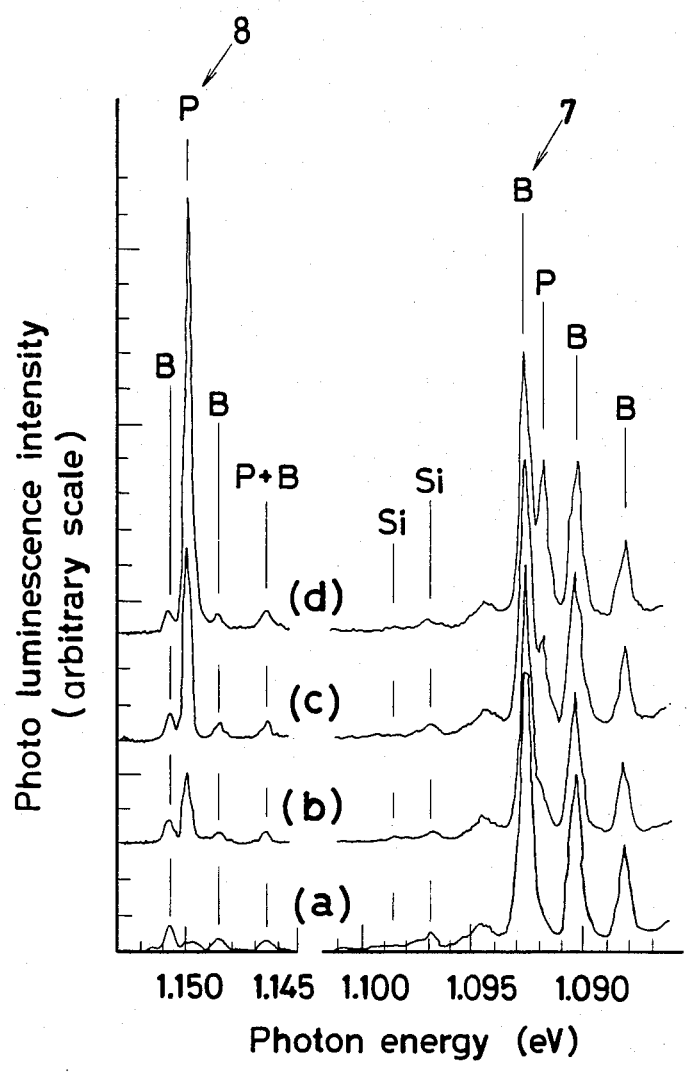
Fig_2

METHOD FOR DETERMINING IMPURITIES IN EPITAXIAL SILICON CRYSTALS

FIELD OF THE INVENTION

The present invention relates to a method for analyzing concentrations and kinds of impurities in epitaxial silicon crystals generally used in the present-day silicon device process.

BACKGROUND OF THE INVENTION

At present, epitaxial silicon crystals grown on a silicon crystal substrate are widely used for devices such as ICs, LSIs, and the like. Since impurities in the epitaxial crystals greatly influence the characteristics, yields and reliability of the devices, analysis of the impurities is very important.

However, a normal epitaxial crystal is very thin, from a few $\mu$m to several tens of $\mu$m, and it is extremely difficult to analyze the impurities in the epitaxial crystals.

Methods for determining concentrations of impurities in crystals heretofore adopted include the resistivity method and the capacitance-voltage method.

However, both of these methods are merely applicable to the determination of concentrations of impurities most abundantly contained in the epitaxial crystals and cannot determine the kinds of the impurities. Accordingly, these methods are quite incapable of being used to assay minute amounts of residual impurities. Using the activation analysis or the secondary ion mass spectroscopy, it is possible to determine the kinds and concentrations of a number of kinds of impurities. However, the sensitivity of these methods is only about $10^{16}$ atmos/cm$^3$ even with respect to typical impurities such as boron, phosphorus, and the like, which is far too low.

With the recent trend toward high integration and high precision in silicon devices, the importance of precise analysis of minute amounts of impurities in epitaxial crystals has increased greatly, but there has not been any known method which can directly detect various impurities in epitaxial crystals in the range of concentration less than $10^{16}$ atoms/cm$^3$.

OBJECT OF THE INVENTION

This invention has been achieved in view of the foregoing, and it is an object of the invention to provide a method for determining the respective concentrations of a number of kinds of impurities contained in epitaxial crystals, non-destructively, simply and with high accuracy.

SUMMARY OF THE INVENTION

In accordance with the present invention, an epitaxial silicon crystal grown on a silicon crystal substrate is irradiated with a laser beam at the temperature of liquid helium to thereby cause the crystal to radiate luminescent light, the spectrum of which varies with the concentration and kind of the impurities in the crystal. This spectrum is analyzed to find the concentration and kind of the impurities. By this method even trace amounts of impurities can be detected non-destructively.

BRIEF DESCRIPTION OF THE DRAWINGS

Other objects and features of the invention will be apparent to those skilled in the art from the disclosure made in the following description of a preferred embodiment of the invention, as illustrated in the accompanying sheets of drawings, in which:

FIG. 1 illustrates the principle of the method for determining the concentration of an impurity in an epitaxial silicon crystal in accordance with the present invention;

FIG. 2 is a spectral graph showing the luminescence spectram of epitaxially grown layers containing various concentrations of phosphorus formed on crystal substrates (b,c,d) and a spectrum of the substrate (a);

FIG. 3 is a graph showing the relationship between the luminescence intensity ratio and the phosphorus concentration in an epitaxial crystal containing phosphorus;

FIG. 4 is a graph showing the relationship between the luminescence intensity ratio and the arsenic concentration in an epitaxial crystal to which arsenic has been added; and FIG. 5 is a spectral graph showing the luminescence spectrum of an epitaxially grown layer simultaneously containing phosphorus, aluminum and arsenic formed on a crystal substrate.

DETAILED DESCRIPTION OF THE PREFERRED EMBODIMENT

FIG. 1 illustrates the principle of the method for determining the concentration of an impurity in an epitaxial silicon crystal in accordance with the present invention. A specimen having an epitaxial silicon crystal 1 grown on a silicon crystal substrate 2 is cooled to the temperature of liquid helium and a laser beam 3 is directed onto the surface of the epitaxial crystal 1. When the specimen is irradiated by the laser beam, excess electrons and holes are produced therein and diffused within the range of the diffusion length (broken line 4). A portion of these excess electrons and holes recombine within the epitaxial crystal 1 to emit luminescent light 5, whereas the remaining portion are diffused into the substrate 2 where they recombine to emit luminescent light 6. The luminescent light 5 from the epitaxial crystal 1 and the luminescent light 6 from the substrate 2 respectively contain information regarding impurities in the epitaxial crystal and substrate. That is, considering the case where two epitaxial crystal layers, different in concentration of an impurity, are grown on the same kind of crystal substrate, if the layers of the epitaxially grown crystals have the same thickness, the luminescent light from the substrate will be of substantially the same intensity but the intensity of the luminescent light from the epitaxial crystal layers will vary depending on their respective impurity concentrations. Accordingly, the concentration of the impurity in the epitaxial crystals can be obtained from the amount of variation in intensity.

If the kind of the impurities is different, the luminescent spectra resulting from the impurities will differ, and therefore, it is possible to know the kind of the impurity according to the position of the spectral peaks.

In this invention the specimen to be tested is cooled to the temperature of liquid helium in order to utilize the luminescence resulting from bound exciton at the impurity. When the temperature increases, the bound exciton is released from the impurity. Thus, it is necessary to test the specimen at the liquid helium temperature of $T \leq 5K$.

Laser beams usable for irradiating specimens include the known Ar ion laser and Kr ion laser. With respect to the intensity of the laser beam, if the epitaxial crystal layer is thick, the luminescent light from the substrate becomes weak. In such a case, the laser beam intensity must be increased to a degree that the luminescent light from the substrate can be detected.

FIG. 2 shows an example of the luminescent spectra measured on epitaxial crystals at the temperature of liquid helium.

The laser used for the measurement was an Ar ion laser (wavelength, 514.5 nm), the intensity of the laser beam on the sample surface was 300 mW, the diameter of the beam is 2.5 mm, and the angle of irradiation of the beam with respect to the specimen surface was about 80°. The spectrometer used had a focal length of 0.75 m, an F-value of 7.0, and a diffraction grating having 600 grooves/mm and a Blaze wavelength of 1.25 $\mu$m. The detector used is a photomultiplier (S1 photocathode).

Shown by (a) in FIG. 2 is a spectrum of a crystal substrate having no epitaxial crystal grown thereon and containing boron of $4 \times 10^{14}$ atoms/cm$^3$. Denoted by (b), (c) and (d) in FIG. 2 are the spectra of three specimens wherein an epitaxial crystal of a thickness of 2.5 $\mu$m was grown on the aforesaid crystal substrate, phosphorus being added as an impurity thereto at the concentration of $1.6 \times 10^{15}$, $4 \times 15^{15}$ and $1.5 \times 10^{16}$ atoms/cm$^3$. The peaks of these spectra are indicated by the atomic symbol of the impurity which caused the luminescence.

It is to be noted that the peak indicated by Si is the luminescence inherent in silicon, not due to impurities. The patterns of the luminescent components caused by boron in the spectra (b), (c) and (d) are exactly the same as that of the spectrum (a) of the crystal substrate and are understood to be from the substrate. Also, the luminescent components caused by phosphorus appearing in spectra (b), (c) and (d) have intensities which increase as the concentration of phosphorus increases. Here, the result obtained by examining the relationship between the intensity ratio between the luminescent component 7 caused by boron in the substrate and the luminescent component 8 caused by phosphorus in the epitaxial crystal, and the phosphorus concentration is given in FIG. 3. As shown in FIG. 3, there is a fixed relation between the intensity ratio and the impurity concentration, and therefore, if said relation is preexamined, the impurity concentration in the epitaxial crystal can be obtained from the intensity ratio of the luminescent spectra making use of the aforesaid relation. The result obtained by examining similar relation with respect to arsenic impurity is shown in FIG. 4. FIG. 4 also shows a fixed relationship over a wide range concentration. While in the foregoing, the case in which the impurities in the epitaxial crystal are of one same kind has been illustrated, it should be understood that even in the case of a number of kinds of impurities, the luminescent spectra caused by the respective impurities independently appear, and the above-described method can be used for analysis.

In this embodiment, an epitaxial crystal of a thickness of about 3 $\mu$m was grown on a crystal substrate containing boron of an amount of about $4 \times 10^{14}$ atoms/cm$^3$. This specimen was cooled to the temperature of liquid helium and similarly to the case of FIG. 2, an Ar ion laser beam was directed onto the surface of the epitaxial crystal to obtain a photo-luminescent spectrum, which is shown in FIG. 5.

As is apparent from FIG. 5, the respective peaks are seen with respect to phosphorus, aluminum and arsenic not contained in the substrate, and it is presumed from the said spectral view that in the epitaxially grown layer, the phosphorus concentration was $10^{13}$–$10^{14}$ atoms/cm$^3$, the Al concentration $10^{12}$–$10^{13}$ atoms/cm$^3$ and the arsenic concentration $10^{14}$ atoms/cm$^3$.

As described hereinbefore, the method for determining the concentrations of impurities in an epitaxial silicon crystal in accordance with the present invention may be applied to non-destructively detect impurities contained at about $10^{13}$–$10^{16}$ atoms/cm$^3$ in a thin epitaxial crystal having a thickness of a few $\mu$m and to determine the concentrations and kinds thereof. This was not at all possible by conventional techniques.

The method of the present invention may be applied to the actual process for producing silicon epitaxial crystals in order to accurately grasp the auto-doping effect from the substrate in question in said process and the contamination status from various elements within a reaction furnace, thus greatly contributing to the improvement of the process, and to the enhancement of characteristics of the devices produced as well as their yield and reliability.

Obviously, many modifications and variations of the present invention are possible in light of the above teachings. It is therefore to be understood that within the scope of the appended claims, the present invention may be practiced otherwise than as specifically described herein.

What is claimed is:

1. A method for determining impurities within an epitaxial silicon crystal grown upon a silicon crystal substrate, comprising the steps of:
   irradiating the surface of an epitaxial silicon crystal grown upon a silicon crystal substrate with a laser beam at the temperature of liquid helium so as to result in the emanation of luminescent light beams from said epitaxial silicon crystal and said silicon crystal substrate in response to the presence of impurities within said epitaxial silicon crystal and said silicon crystal substrate;
   obtaining spectra of said luminescent light beams emanating from said epitaxial silicon crystal and said silicon crystal substrate; and
   forming a relationship between the photo luminescence intensity ratio of the photo luminescence intensity of said luminescent light beam from said epitaxial silicon crystal to the photo luminescence intensity of said luminescent light beam from said silicon crystal substrate, as derived from said spectra of said luminescent light beams emanating from said epitaxial silicon crystal and said silicon crystal substrate, and the concentration of said impurity within said epitaxial silicon crystal, whereby the concentration of said impurity within said epitaxial silicon crystal may be determined from said relationship as a function of said photo luminescence intensity ratio.

2. A method as set forth in claim 1, wherein:
   said laser beam is transmitted from an argon ion laser.

3. A method as set forth in claim 1, wherein:
   said laser beam is transmitted from a krypton ion laser.

4. A method as set forth in claim 1, wherein:
   said relationship is a graphical representation of said ratio and epitaxial silicon crystal impurity concentration values.

5. A method as set forth in claim 4, wherein:
   said photo luminescence intensity ratio is plotted along the ordinate axis of said graphical representation; and
   said impurity concentration is plotted along the abscissa axis of said graphical representation.

* * * * *